US00PP07798P

United States Patent [19]

Drewlow

[11] Patent Number: Plant 7,798

[45] Date of Patent: Feb. 18, 1992

[54] KALANCHOE PLANT NAMED KEEPSAKE

[75] Inventor: Lyndon W. Drewlow, Ashtabula, Ohio

[73] Assignee: Mikkelsens, Inc., Ashtabula, Ohio

[21] Appl. No.: 607,442

[22] Filed: Oct. 31, 1990

[51] Int. Cl.[5] ..... A01H 5/00
[52] U.S. Cl. ..... Plt./68
[58] Field of Search ..... Plt./68

*Primary Examiner*—James R. Feyrer
*Attorney, Agent, or Firm*—Foley & Lardner

[57] ABSTRACT

A new and distinct cultivar of Kalanchoe plant named Keepsake, characterized by its large, scarlet red flowers, flowering time of 10–11½ weeks, dark green, shallow cut crenate leaves, excellent lateral and basal branching, a mounded growth habit, and superior inflorescence.

1 Drawing Sheet

The present invention relates to a new and distinctive cultivar of Kalanchoe plant, botanically known as Kalanchoe, and known by the cultivar name Keepsake. Keepsake was developed by me through controlled breeding by crossing Attraction (seed parent) with Avanti (pollen parent). Attraction is disclosed in U.S. Plant Pat. No. 5,888, and Avanti is disclosed in U.S. Plant Pat. No. 5,962.

Asexual reproduction by stem cuttings has shown that the unique features of this new Kalanchoe are stabilized and are reproduced true to type in successive propagations.

The following characteristics distinguish Keepsake from both its parent varieties and other cultivated Kalanchoes of this type known and used in the floriculture industry, including the female or seed parent Attraction, and the comparison cultivar Garnet, disclosed in U.S. Plant Pat. No. 6,631.

1. The flower color of Keepsake is scarlet red (42A), compared to the orange-red (40A) flower color of Attraction and the crimson red (44A) flower color of Garnet.

2. Keepsake is 7 days later to flower than Attraction but 7 days earlier to flower than Garnet under summer conditions. Under winter conditions Attraction and Keepsake are similar in flowering response, but 7 days earlier than Garnet from the start of short day treatment.

3. Average flower diameter of Keepsake is 16 mm while Attraction has an average flower diameter of 18 mm and Garnet 15 mm.

4. Average height of Attraction and Keepsake are similar at 18 to 19 cm, while Garnet is taller at 21 to 22 cm.

5. Attraction and Keepsake have similar colored (dark green) and similarly shaped leaves with shallow-cut crenate leaves. Garnet has a darker green leaf that is more deeply cut and not as finely crenate. The leaves of Garnet are also more rounded than Keepsake and Attraction. Attraction has foliar disease problems which Keepsake does not have.

6. Keepsake has lateral and basal branching from each node to soil line, while Attraction and Garnet are not as heavily basal branched or lateral branched.

7. Keepsake and Attraction have a mounded growth habit while Garnet has more of an upright habit of growth.

8. Because of its basal and lateral branching the inflorescence of Keepsake has many more individual flowers than either Garnet or Attraction.

9. Peduncle of main stem of Keepsake just below the first major branch in the inflorescence is between 3 and 4 mm in diameter, while the peduncles of Attraction and Garnet are between 4 and 5 mm in diameter.

The accompanying colored photograph illustrates in front perspective view the overall appearance of Keepsake, showing the colors as true as it is reasonably possible to obtain in a colored reproduction of this type. The photograph was taken on Mar. 23, 1990 under natural light on an overcast day, and under double poly greenhouse covering at Ashtabula, Ohio.

The following is a detailed description of my new cultivar, based on plants produced in greenhouses in Ashtabula, Ohio during the late spring to summer season of the year. Plants were grown in 10 cm pots and measurements were taken 12 weeks after rooted cuttings were planted. Height measurements were taken from the soil line of the container. The plants were grown at 65°–68° F. night temperatures, under 3500–4000 foot candles of light, and 240 ppm nitrogen, 240 ppm potassium, and 175 ppm phosphorous nutritional levels with trace elements added. 5000 ppm B-9 was applied week three and week five of short day treatment of the six week short day treatment (14 hours dark) period. Habit of growth, plant height, flowering time, size of leaves and peduncle length will be greatly influenced by nutritional and environmental conditions.

Colors references are made to The Royal Horticultural Society Colour Chart except where general terms of ordinary dictionary significance are used.

Parentage: A controlled cross between female parent Attraction and male parent Avanti.

Propagation:

(A) *Type cutting.*—Stem tip cutting up to 3 cm long.

(B) *Time to root.*—10 days at 21° C. in summer; 14 days at 21° C. in winter.

(C) *Rooting habit.*—Abundant roots, fine, fibrous.

Plant description:

(A) *Habit and form of growth.*—Compact; semi-mounded because of excellent basal branching; flower clusters are held above foliage. Environment and use of growth regulators will play a role in final height. Laterals and main stem very similar in length.

(B) *Foliage description.*—Leaves simple and opposite. 1. Size: Average; full grown leaves on a plant grown in a 10 cm pot are 9.5 to 10.5 cm long and 7.5 to 8.0 cm wide. 2. Shape: Ovate, apex obtuse; base rounded to acute. 3. Texture: Glabrous, coriaceous, and succulent. 4. Margin: Crenate; shallow lobed. 5. Color: Young foliage, top side 146A; under side 146B. Mature foliage, top side 146A; underside 147B.

Flowering description:

(A) *Flowering habit.*—Inflorescence is a cyme. Terminal flower on main axis opens first, followed by the terminal flowers of the side branches, and continuing with the subsequent development of branches in the inflorescence. Inflorescence is made up of the main stem and up to six or more lateral branches. Lateral branches in this cultivar are almost as large as main stem.

(B) *Natural flowering season.*—Early January. Flowering time under controlled daylength at 20° C. in summer is 10 weeks; in winter 11½ weeks. Flowering time depends on temperature, light intensity and other growing conditions.

(C) *Flower buds.*—Oblong, up to 4 mm long before showing color, developing tubular as flower petals mature; sheathed in four green sepals.

(D) *Flowers borne.*—On compound dichasil cymes, primary peduncle 3 mm in diameter just below first branch of the inflorescence; length will vary depending on growing conditions. Pedicels vary in length depending on where they are located in the inflorescence.

(E) *Quantity of flowers.*—Very floriferous, with main stem and five or more laterals having 60 or more flowers each.

(F) *Petals.*—1. Shape: Almost rounded top cuspidate. 2. Color: Top side when opening 42A, fading to 46C; under side 43D. 3. Number of petals: Four. 4. Size: Individual petals 5.5 mm wide and 7 mm long; flowers 16 mm in diameter.

Reproductive organs:

1. *Stamens.*—Eight in number. a. Anther shape: Flat, elliptical, color yellow green. b. Filament color: Yellow green. c. Pollen color: Yellow.
2. *Pistils.*—a. Stigma shape: Flat, mature color whitish. b. Style color: Yellow green. c. Ovaries: Four in number; size 5 mm; color green.

Disease resistance: Keepsake has shown resistance to Powdery Mildew and no other disease problems have been noted to date.

Other important characteristics: Keepsake is part of a series of Kalanchoe plants that include Majestic, Splendor, Revelry and Heirloom (all disclosed in pending plant patent applications of applicant) that are similar in flowering time, height, branching and response to growth regulators. This allows greenhouse growers to handle all five distinctly different colors at the same time from a single planting date and use the same growing methods on each to end up with a uniform crop. The end results are easier crops for the growers to produce and higher quality crops. All cultivars are ideal for both 10 and 15 cm pot production.

I claim:

1. A new and distinct cultivar of Kalanchoe plant named Keepsake, as illustrated and described.

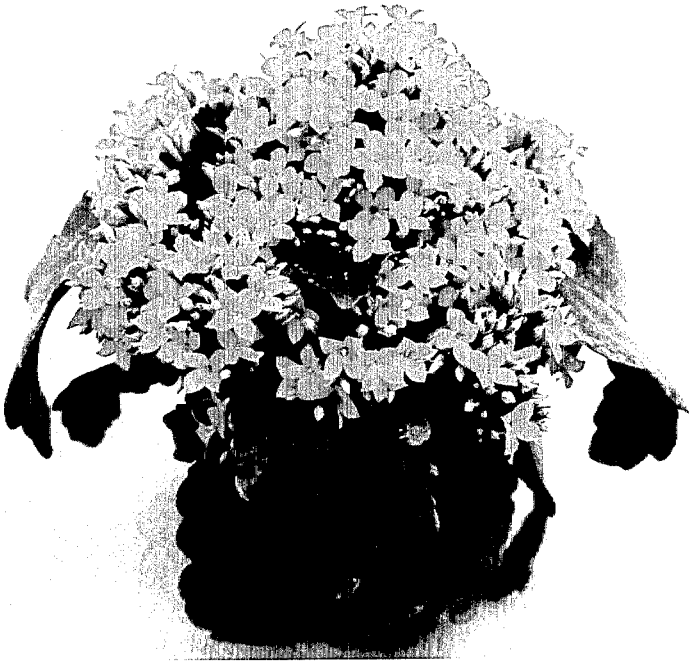

* * * * *